United States Patent
Ueda et al.

(10) Patent No.: US 9,789,345 B2
(45) Date of Patent: Oct. 17, 2017

(54) WATER-IN-OIL EMULSION SUNSCREEN COSMETIC COMPOSITION

(75) Inventors: Hideto Ueda, Yokohama (JP); Koji Abe, Yokohama (JP); Akio Nasu, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 13/146,418

(22) PCT Filed: Jan. 27, 2010

(86) PCT No.: PCT/JP2010/051008
§ 371 (c)(1),
(2), (4) Date: Feb. 8, 2012

(87) PCT Pub. No.: WO2010/087354
PCT Pub. Date: Aug. 5, 2010

(65) Prior Publication Data
US 2012/0134939 A1    May 31, 2012

(30) Foreign Application Priority Data

Jan. 27, 2009 (JP) ................................ 2009-015023

(51) Int. Cl.
| | | |
|---|---|---|
| A61Q 17/04 | (2006.01) | |
| A61K 8/03 | (2006.01) | |
| A61K 8/06 | (2006.01) | |
| A61K 8/73 | (2006.01) | |
| A61K 8/99 | (2017.01) | |

(52) U.S. Cl.
CPC ............... *A61Q 17/04* (2013.01); *A61K 8/03* (2013.01); *A61K 8/06* (2013.01); *A61K 8/064* (2013.01); *A61K 8/73* (2013.01); *A61K 8/99* (2013.01); *A61K 2800/882* (2013.01)

(58) Field of Classification Search
CPC . A61K 8/03; A61K 8/06; A61K 8/064; A61K 8/99; A61K 2800/882; A61K 8/73; A61Q 17/04
See application file for complete search history.

(56) References Cited

U.S. PATENT DOCUMENTS

| | | |
|---|---|---|
| 2001/0021375 A1 | 9/2001 | Hossel et al. |
| 2002/0058053 A1 | 5/2002 | Nakanishi et al. |
| 2005/0118211 A1 | 6/2005 | Nakamura et al. |
| 2008/0305056 A1* | 12/2008 | Jenni et al. ............ 424/59 |
| 2009/0098169 A1* | 4/2009 | Ootake ............ A61K 8/06 424/401 |

FOREIGN PATENT DOCUMENTS

| | | |
|---|---|---|
| JP | 2001055307 A2 | 2/2001 |
| JP | 2001226222 | 8/2001 |
| JP | 2001226222 A2 | 8/2001 |
| JP | 2002212028 A2 | 7/2002 |
| JP | 2002255738 | 9/2002 |
| JP | 2002255738 A2 | 9/2002 |
| JP | 2002363029 | 12/2002 |
| JP | 2002363029 A2 | 12/2002 |
| JP | 2006248999 | 9/2006 |
| JP | 2006248999 A2 | 9/2006 |
| JP | 2007045760 | 2/2007 |
| JP | 2007161648 | 6/2007 |
| JP | 2007161648 A2 | 6/2007 |
| JP | 2007217361 | 8/2007 |
| JP | 2007217361 A2 | 8/2007 |
| JP | 2008195693 | 8/2008 |
| JP | 2008195693 A2 | 8/2008 |

OTHER PUBLICATIONS

Sworn et al., Gums and Stabilizers for the Food Industry, 16, 89-97 (2012).*
Espacenet Bibliographic Data for patent abstract JP 2007161648 published Jun. 28, 2007, one page.
Espacenet Bibliographic Data for patent abstract JP 2007217361 published Aug. 30, 2007, one page.
Espacenet Bibliographic Data for patent abstract JP 2008195693 published Aug. 28, 2008, one page.
Espacenet Bibliographic Data for patent abstract JP 2001226222 published Aug. 21, 2001, one page.
Espacenet Bibliographic Data for patent abstract JP 2002255738 published Sep. 11, 2002, one page.
Espacenet Bibliographic Data for patent abstract JP 2006248999 published Sep. 21, 2006, one page.
Espacenet Bibliographic Data for patent abstract JP 2002363029 published Dec. 18, 2002, one page.
Espacenet Bibliographic Data for patent abstract JP 2007045760 published Feb. 22, 2007, one page.

* cited by examiner

*Primary Examiner* — Robert Cabral
(74) *Attorney, Agent, or Firm* — Rankin, Hill & Clark LLP

(57) ABSTRACT

To provide a low-viscosity water-in-oil emulsion sunscreen cosmetic composition which is extremely excellent in UV protective enhancing effect (as the protective boosting effect of the UV absorption capability thereof) over a broad UV radiation region and has superior feeling in use (smooth feeling, dry feeling, and non-sticky feeling, etc.). A water-in-oil emulsion sunscreen cosmetic composition comprising (a) from 0.01 to 10% by mass of a water-soluble polymer and (b) from 0.01 to 30% by mass of a UV absorbent, and having a viscosity of at most 10,000 mPa·s (as measured with a B-type viscometer at 30° C.), wherein the aqueous phase accounts for at most 45% by mass.

11 Claims, No Drawings

WATER-IN-OIL EMULSION SUNSCREEN COSMETIC COMPOSITION

TECHNICAL FIELD

The present invention relates to a water-in-oil emulsion sunscreen cosmetic composition. More precisely, the invention relates to a low-viscosity water-in-oil emulsion sunscreen cosmetic composition which is extremely excellent in enhancing ultra-violet (=UV) protective effect over a broad UV radiation region and has superior feeling in use (smooth feeling, dry feeling, and non-sticky feeling, etc.).

BACKGROUND ART

As the important UV radiation absorption wavelength region for a sunscreen cosmetic composition, it includes a UV-A region (320 to 400 nm) and a UV-B region (290 to 320 nm). Heretofore, it has been considered that the UV radiation in a UV-A region could cause darkening or tanning of the skin but would not cause sunburn, thereby to promote skin aging like the UV radiation in a UV-B region. Recently, however, it has become known that the UV-B radiation could stay relatively in the surface part of the skin while the UV-A radiation could reach the deep part of the skin to be therefore a cause of inducing not only skin aging but also skin cancer. Accordingly, a sunscreen cosmetic composition has become desired that exhibits an UV protective effect over a broad UV radiation region covering both the UV-B region and the UV-A region.

Especially with the recent skin-whitening boom, a sunscreen cosmetic composition much more excellent in the UV protective effect than before has become desired these days. Products additionally satisfying excellent feeling in use (non-sticky feeling, etc.) are more preferred. Further desired are low-viscosity ones that are lightly spreadable in application thereof.

As techniques close to the sunscreen cosmetic composition of the present invention, there may be exemplified ones described in the following Patent References 1 to 3.

Specifically, JP 2008-162930A (Patent Reference 1) describes an oil-in-water emulsion sunscreen cosmetic composition containing an oil-soluble UV absorbent, a water-soluble thickening agent (for example, acrylic water-soluble polymer, etc.), a water-soluble UV absorbent, and a specific hydrophilic nonionic surfactant, saying that the cosmetic composition is excellent in UV protective capability and stability, without detracting from the fresh-feeling thereof. The sunscreen cosmetic composition described in Patent Reference 1 secures the fresh-feeling thereof as being an oil-in-water emulsion, but on the contrary, has an undeniable defect in that its waterproofness is not sufficient as compared with a water-in-oil emulsion one.

JP 2007-217379A (Patent Reference 2) describes a water-in-oil emulsion sunscreen cosmetic composition which exhibits an excellent UV screening effect and an effect of preventing/inhibiting odor change with the passage of time and which is prepared by incorporating a neutralized salt of phenylbenzimidazolesulfonic acid into the aqueous phase (inner phase) of a water-in-oil emulsion system combined with an oily phase (outer phase) composed of octocrylene and hydrophobicated titanium dioxide and/or zinc oxide. However, Patent Reference 2 has neither description nor suggestion indicating that the water-in-oil emulsion sunscreen cosmetic composition could dramatically enhance the UV absorption capability thereof, as the boosting effect of the UV absorption capability thereof, owing to the combined use of the UV absorbent and the water-soluble polymer therein.

JP 2007-291094A (Patent Reference 3) describes a water-in-oil emulsion sunscreen cosmetic composition that comprises, as incorporated therein, surface-treated zinc oxide of which the surface is coated with (dimethicone/methicone) copolymer and an organic titanate and/or trialkoxyalkylsilane, saying that the cosmetic composition is excellent in spreadability and is excellent in the dispersion stability of the powder form thereof with the passage of time and in the UV protective effect. However, also in this Patent Reference 3, there is given neither description nor suggestion indicating that the water-in-oil emulsion sunscreen cosmetic composition could dramatically enhance the UV absorption capability thereof (as the protective boosting effect of the UV absorption capability thereof) owing to the combined use of the UV absorbent and the water-soluble polymer therein.

PRIOR ART REFERENCES

Patent References

Patent Reference 1: JP 2008-162930A
Patent Reference 2: JP 2007-217379A
Patent Reference 3: JP 2007-291094A

SUMMARY OF THE INVENTION

Problems that the Invention is to Solve

An object of the invention is to provide a low-viscosity water-in-oil emulsion sunscreen cosmetic composition which is extremely excellent in enhancing UV protective effect over a broad UV radiation region and has excellent feeling in use (smooth feeling, dry feeling, and non-sticky feeling, etc.).

Means for Solving the Problems

Heretofore, in a water-in-oil emulsion system, it has been considered that, when an aqueous ingredient having a large molecular weight such as a water-soluble polymer or the like is incorporated in the aqueous phase that serves as a disperse phase, then it may worsen the feeling in use of the system owing to the sticky feeling that results from the water-soluble polymer and may worsen the stability (balance of the system) thereof, and for these reasons, in general, a water-soluble polymer is not positively incorporated in the aqueous phase.

This time given the situation, the present inventors have made assiduous studies for solving the above-mentioned problems in the related art, and as a result, have found that, when a water-soluble polymer is incorporated in the aqueous phase of a water-in-oil emulsion sunscreen cosmetic system with an UV absorbent incorporated therein, then surprisingly, the UV absorption capability of the system significantly increases over a broad UV radiation region (as the protective boosting effect of the UV absorption capability thereof) and the feeling in use of the system is also excellent, and have completed the present invention.

Specifically, the invention provides a water-in-oil emulsion sunscreen cosmetic composition comprising (a) from 0.01 to 10% by mass of a water-soluble polymer and (b) from 0.01 to 30% by mass of an UV absorbent, and having a viscosity of at most 10,000 mPa·s (as measured with a B-type viscometer at 30° C.), wherein the aqueous phase accounts for at most 45% by mass.

Advantage of the Invention

According to the invention, there is provided a low-viscosity water-in-oil emulsion sunscreen cosmetic composition which is extremely excellent in enhancing UV protective effect (as the protective boosting effect of the UV absorption capability thereof) over a broad ultraviolet radiation region and having superior feeling in use (smooth feeling, dry feeling, and non-sticky feeling, etc.).

MODE FOR CARRYING OUT THE INVENTION

The water-in-oil emulsion sunscreen cosmetic composition of the invention is described in detail hereinunder.

The water-soluble polymer as component (a) includes natural water-soluble polymers, semisynthetic water-soluble polymers, synthetic polymers, and inorganic water-soluble polymers.

Examples of the natural water-soluble polymers include plant-derived water-soluble polymers, such as gum arabic, tragacanth gum, galactan, guar gum, locust bean gum, tamarind bum, carob gum, karaya gum, carrageenan, pectin, agar, quince seed (Marmelo), algae colloid (Phaeophyceae-extract), starch (rice, corn, potato, wheat), and glycyrrhizinate; microorganism-derived water-soluble polymers, such as xanthan gum, dextran, succinoglycan, and pullulan; animal-derived water-soluble polymers, such as collagen, casein, albumin, and gelatin.

Examples of the semisynthetic water-soluble polymers include starch-type water-soluble polymers, such as carboxymethyl starch, and methylhydroxypropyl starch; cellulose-type water-soluble polymers, such as methyl cellulose, nitrocellulose, ethyl cellulose, methylhydroxypropyl cellulose, hydroxyethyl cellulose, cellulose sodium sulfate, hydroxypropyl cellulose, carboxymethyl cellulose (CMC), crystalline cellulose, and cellulose powder; alginate-type water-soluble polymers, such as sodium alginate, and propylene glycol alginate.

Examples of the synthetic water-soluble polymers include vinylic water-soluble polymers, such as polyvinyl alcohol, polyvinyl methyl ether, polyvinyl pyrrolidone, and carboxyvinyl polymer (Carbopol); polyoxyethylene-type water-soluble polymers, such as Polyethylene Glycol 20,000, 4,000,000, and 600,000; copolymer-type water-soluble polymers such as polyoxyethylene polyoxypropylene copolymer; acrylic water-soluble polymers, such as sodium polyacrylate, polyethyl acrylate, and polyacrylamide; as well as polyethyleneimine, and cationic polymer.

Examples of the inorganic water-soluble polymers include bentonite, AlMg silicate (Veegum), laponite, hectorite, and silicic anhydride.

One or more types may be used as component (a). Among these, natural water-soluble polymers are favorably used from the viewpoint of the enhancing UV protective effect of the cosmetic composition; and more preferred are plant-derived water-soluble polymers and microorganism-derived water-soluble polymers. Above all, especially preferred are agar and succinoglycan.

The amount of component (a) is from 0.01 to 10% by mass in the cosmetic composition of the invention, preferably from 0.05 to 5% by mass, more preferably from 0.1 to 1% by mass. When the amount is less than 0.01% by mass, then the enhancing UV protective effect is difficult to attain; but on the other hand, when the component is incorporated in an amount more than 10% by mass, then the feeling in use and the stability of the preparation may be worsened.

Not specifically defined, the UV absorbent as component (b) may be any one capable of being incorporated in cosmetic compositions, and may be any of oil-soluble ones or water-soluble ones.

The oil-soluble UV absorbents include benzoic acid-type UV absorbents, such as paraaminobenzoic acid (PABA), PABA monoglyceryl ester, N,N-dipropoxy-PABA ethyl ester, N,N-diethoxy-PABA ethyl ester, N,N-dimethyl-PABA ethyl ester, N,N-dimethyl-PABA butyl ester, and hexyl diethylaminohydroxybenzoylbenzoate; anthranilic acid-type UV absorbents, such as homomenthyl-N-acetyl anthranilate; salicylic acid-type ultraviolet absorbents. such as amyl salicylate, menthyl salicylate, homomenthyl salicylate, octyl salicylate, phenyl salicylate, benzyl salicylate, and p-isopropanolphenyl salicylate; cinnamic acid-type UV absorbents, such as octyl cinnamate, ethyl 4-isopropylcinnamate, methyl 2,5-diisopropylcinnamate, ethyl 2,4-diisopropylcinnamate, methyl 2,4-diisopropylcinnamate, propyl-p-methoxycinnamate, isopropyl-p-methoxycinnamate, isoamyl-p-methoxycinnamate, octyl-p-methoxycinnamate [=2-ethylhexyl-p-methoxycinnamate], 2-ethoxyethyl-p-methoxycinnamate, cyclohexyl-p-methoxycinnamate, ethyl-$\alpha$-cyano-$\beta$-phenylcinnamate, 2-ethylhexyl-$\alpha$-cyano-$\beta$-phenylcinnamate, glyceryl mono-2-ethylhexanoyl-diparamethoxycinnamate, and 3-methyl-4-[methylbis(trimethylsiloxy)silyl]butyl 3,4,5-trimethoxycinnamate; 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenylbenzotriazole), dibenzaladine, dianisoylmethane, 4-tert-butyl-4'-methoxydibenzoylmethane, 4-(1,1-dimethylethyl)-4'-methoxydibenzoylmethane, 5-(3,3-dimethyl-2-norbornylidene)-3-pentan-2-one, octocrylene [=2-ethylhexyl 2-cyano-3,3-diphenyl-2-propenoate], and Polysilicone-15 [=dimethicodiethylbenzal malonate], but not limited thereto. Above all, preferred ones are benzoic acid-type UV absorbents, silicic acid-type ultraviolet absorbents, octocrylene and Polysilicone-15 and the like, from the viewpoint of the ability of ultraviolet radiation protection enhancement when combined with component (a).

The water-soluble UV absorbents include benzophenone-type UV absorbents, such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonic acid salt, 4-phenylbenzophenone, 2-ethylhexyl 4'-phenyl-benzophenone-2-carboxylate, 2-hydroxy-4-n-octoxybenzophenone, and 4-hydroxy-3-carboxybenzophenone; benzimidazole-type UV absorbents, such as phenylbenzimidazole-5-sulfonic acid and its salts, phenylene-bis-benzimidazole-tetrasulfonic acid and its salts; benzotriazole-type UV absorbents such as methylene-bis-benzotriazolyl-tetramethylbutylphenol; 3-(4'-methylbenzylidene)-d,l-camphor, 3-benzylidene-d,l-camphor, urocanic acid, and ethyl urocanoate, etc. However, the invention is not limited to these exemplifications. Above all, preferred for use herein are benzimidazole-type UV absorbents, benzotriazole-type UV absorbents and the like, from the viewpoint of enhancement of UV protection when combined with component (a).

The amount of component (b) is from 0.01 to 30% by mass in the cosmetic composition of the invention, preferably from 0.1 to 20% by mass, more preferably from 1 to 10% by mass. When the amount is less than 0.01% by mass, then the enhancement of the UV radiation protective effect is difficult to attain sufficiently; but on the other hand, when the component is incorporated in an amount more than 30% by mass, then the feeling in use as well as the stability and the safety of the preparation may be worsened. One or more types may be used as component (b).

The water-in-oil emulsion sunscreen cosmetic composition of the invention contains component (a) and component (b); however, heretofore, component (a) has not been positively incorporated into water-in-oil emulsion systems because of the feeling in use (sticky feeling, etc.) thereof. In the water-in-oil emulsion system of the present invention, component (a) is incorporated as combined with component (b) therein, whereby the system exhibits the effect of much more enhancing the UV radiation absorption capability of component (b) (as the boosting effect of the UV absorption capability thereof), which is an extremely excellent effect that could not be heretofore anticipated. Accordingly, even when the amount of component (b) therein is lower than before, the cosmetic composition of the present invention attains the UV radiation protective effect much more excellent than that of ordinary cosmetic compositions where the incorporation level of component (b) therein is high. In addition, the cosmetic composition of the present invention has improved the feeling in use thereof, nor having oily feeling, sticky feeling and the like which water-in-oil emulsions systems often have in their application to the skin. Accordingly, the present invention has succeeded in satisfying both the significant improvement of the UV protective effect and the feeling in use of the cosmetic composition.

The water-in-oil emulsion sunscreen cosmetic composition of the invention may further contain a hydrophobic powder from the viewpoint of improving the waterproofness of the cosmetic composition. The hydrophobic powder includes not only a powder that is hydrophobic by itself but also even a hydrophilic powder or the like of which the surface is hydrophobicated to be a hydrophobicated powder.

Examples of the hydrophobic powder concretely include organic powders, such as polyamide resin powder (nylon powder), poly-ethylene powder, polymethyl methacrylate powder, polystyrene powder, styrene/acrylic acid copolymer resin powder, benzoguanamine resin powder, polytetrafluoroethylene powder, and cellulose powder; silicone powders such as trimethyl-silsesquioxane powder.

The powder ingredient of the hydrophobicated powder includes inorganic powders, such as talc, kaolin, mica, sericite, muscovite, phlogopite, synthetic mica, lepidolite, biotite, lepidolite, vermiculite, magnesium carbonate, calcium carbonate, aluminium silicate, barium silicate, calcium silicate, magnesium silicate, strontium silicate, metal tungstate, magnesium, silica, zeolite, barium sulfate, fired calcium sulfate (burnt plaster), calcium phosphate, fluoroapatite, hydroxyapatite, ceramic powder, metal soap (zinc myristate, calcium palmitate, aluminium stearate, etc.), and boron nitride; inorganic white pigments, such as titanium dioxide, and zinc oxide; inorganic red pigments, such as iron oxide (Ben gala), and iron titanate; inorganic brown pigments such as γ-iron oxide; inorganic yellow pigments, such as yellow iron oxide, and yellow ocher; inorganic black pigments, such as black iron oxide, carbon black, and low-order titanium dioxide; inorganic violet pigments, such as mango violet, and cobalt violet; inorganic green pigments, such as chromium oxide, chromium hydroxide, and cobalt titanate; inorganic blue pigments, such as ultramarine, and prussian blue; pearl pigments, such as titanium dioxide-coated mica, titanium dioxide-coated bismuth oxychloride, titanium dioxide-coated talc, colored titanium dioxide-coated mica, bismuth oxychloride, and fish scale foil; metal powder pigments, such as aluminium powder, and copper powder. In the present invention, usable are those prepared by hydrophobicating these powdery ingredients.

The hydrophobication treatment may be attained in any method capable of imparting water repellency to the processed powders. Not specifically defined, herein usable are any ordinary surface treatment. methods such as, for example, a vapor phase method, a liquid phase method, an autoclave method, and a mechanochemical method, etc.

For example, when a hydrophobicating agent is added to the starting material powder for the treatment, it maybe added thereto after diluted with a suitable solvent (dichloroethane, chloroform, hexane, ethanol, xylene, and volatile silicone, etc.), or may be directly added thereto. For mixing and stirring the powder and the processing agent, usable are a ball mill, a faujasite ball mill, a vibration ball mill, an attritor, a pot mill, a rod mill, a pan mill, a homomixer, a homodisperser, a Henschel mixer, and a Nauta mixer, etc. Apart from these, also usable here are a method of polymerizing a cyclic organosiloxane on the powder surface at a low temperature not higher than 100° C. according to vapor phase reaction that utilizes the activity of the powder surface (JP 1-54380B), and a method of its modification followed by adding a pendant group such as glycerol monoallyl ether or the like to the Si—H part of the silicon polymer on the powder surface (JP 1-54381B).

The hydrophobication treatment concretely includes treatment with silicones, such as methylhydrogenpolysiloxane, methylhydrogenpolysiloxane/dimethylpolysiloxane copolymer, and dimethylpolysiloxane; treatment with silane compounds, such as octyltriethoxysilane, and hexyltrimethoxysilane; treatment with fatty acids, such as palmitic acid, and stearic acid; metal soap treatment with alkali metal salts or alkaline earth metal salts of the fatty acids; fluorine treatment with perfluoroalkylphosphoric acid diethanolamine salt, perfluoroalkyltrimethoxysilane, etc., but not limited thereto.

The hydrophobic powder is highly water-repellent, and when actually applied to emulsions, it is excellent in effect sustainability as resistant to water and sweat and as most hardly causing makeup deterioration. In addition, the emulsified particles are dense and are most excellent in long-term stability.

One or more different types of those hydrophobic powders may be used here. The hydrophobic powders are not limited to the ingredients exemplified in the above so far as they are hydrophobic powders applicable to ordinary cosmetic compositions. In the present invention, from the viewpoint of ultraviolet radiation protection, hydrophobicated titanium dioxide, zinc oxide and the like are preferred examples. Hydrophobicated titanium dioxide is available, for example, as commercial products of "TTO-S-4" and "TTO-V-4" (both by Ishihara Sangyo Kaisha, Ltd.), "MT-100TV" and "MT-014V" (both by Tayca Corporation), etc. Hydrophobicated zinc oxide is available, for example, as commercial products of "FZO-50" (by Ishihara Sangyo Kaisha, Ltd.), "MZ-700" (by Tayca Corporation) "Z-Cote HP-1" (by BASF Corporation), etc.

In case where the hydrophobic powder is incorporated, its amount is preferably from 0.1 to 50% by mass in the cosmetic composition of the invention, more preferably from 1 to 30% by mass, even more preferably from 3 to 20% by mass. When the amount is less than 1% by mass, then the hydrophobic powder could hardly exhibit its effect; but when more than 50% by mass, then the feeling in use and the stability of the preparation may be worsened.

The water-in-oil emulsion sunscreen cosmetic composition of the present invention has a low viscosity of at most 10,000 mPa·s (as measured with a B-type viscometer at 30° C.), preferably at most 6,000 mPa·s. When the viscosity is more than 10,000 mPa·s, then the viscosity is too high and the cosmetic composition could not well spread when applied to the skin and could not have a good handling feel.

Not specifically defined, the preparation form of the water-in-oil emulsion sunscreen cosmetic composition may be cream, liquid or the like, but is especially preferably in the form of a two-layer separated one which is in two layers when kept statically and is shaken before use. In the emulsion system having such a low viscosity, a water-soluble polymer having a large molecular weight has not been heretofore positively incorporated especially into the aqueous phase therein.

The water-in-oil emulsion sunscreen cosmetic composition of the present invention can be prepared according to an ordinary method, and the method for its emulsification is not specifically defined. For example, employable is a method of heating the aqueous phase and the oily phase separately up to around 70° C., then gradually adding the heated aqueous phase to the oily phase and emulsifying them with an emulsifier, and thereafter cooling the resulting emulsion to room temperature, or the like, to which, however, the invention is not limited. In the invention, the aqueous phase is incorporated in a ratio of at most 45% by mass relative to the whole amount of the cosmetic composition. When the aqueous phase is more than 45% by mass, then the viscosity of the cosmetic composition may be too high.

If desired, any other optional additive ingredients generally usable in external preparations for skin such as cosmetic compositions, drugs and others may be suitably incorporated in the water-in-oil emulsion sunscreen cosmetic composition of the invention within the range not detracting from the advantage of the invention; and the additives include oils and fats, waxes, hydrocarbon oils, higher alcohols, higher fatty acids, synthetic ester oils, surfactants, metal ion sequestrants, lower alcohols, polyalcohols, powder ingredients, saccharides, amino acids, organic amines, polymer emulsions, pH regulators, skin nutrients, vitamins, antioxidants, antioxidation promoters, fragrances, and water.

Organic-modified clay minerals may also be incorporated. The organic-modified clay minerals include dimethyldistearylammonium hectorite (=quaternium-18 hectorite), dimethyldistearylammonium bentonite (=quaternium-18 bentonite), benzyldimethyldistearylammonium hectorite, as well as dioctadecyldimethylammonium salt-modified montmorillonite, octadecyldimethylbenzylammonium salt-modified montmorillonite, and dihexadecyldimethylammonium salt-modified montmorillonite. In case where the organic-modified clay mineral is incorporated, its amount is preferably at most 1% by mass in the cosmetic compositions.

Other ingredients that may be incorporated in the cosmetic composition include antiseptics, such as ethylparaben, and butylparaben; antiinflammatory agents, such as glycyrrhizinic acid derivatives, glycyrrhetinic acid derivatives, salicylic acid derivatives, hinokitiol, zinc oxide, and allantoin; skin-whitening agents, such as saxifrage extract, and arbutin; various extracts, such as Phellodendron bark, Coptis japonica, Lithospermum erythrorhizon, Paeonia lactiflora, Swertia japonica, birch, sage, loquat, ginseng, aloe, Malva sylve, iris, grapes, dove wheat, luffa, lily, saffron, Cnidium officinale, shengjiang, Hypericum erectum, Ononis spinosa, garlic, red pepper, tangerine peel, Angelica acutiloba, and seaweed; activators, such as royal jelly, photosensitive agents, and cholesterol derivatives; blood circulation promoters, such as nonylic acid vanillylamide, benzyl nicotinate, β-butoxyethylnicotinate, capsaicin, zingerone, cantharis tincture, ichthammol, tannic acid, α-borneol, tocopherol nicotinate, inositol hexanicotinate, cyclandelate, cinnarizine, tolazoline, acetylcholine, verapamil, cepharanthine, and γ-oryzanol; antiseborrheics, such as sulfur, and thiantol; antiinflammatory agents, such as tranexamic acid, thiotaurine, and hypotaurine; but not limited thereto.

EXAMPLES

The invention is described in more detail with reference to the following Examples; however, the invention is not limited to the following Examples. The compounding amount is all in terms of % by mass.

1. UV Protective Enhancing Effect, Viscosity

Examples 1 to 8, Control Examples 1 to 8

The UV absorption capability enhancing effect (=the boosting effect of UV absorption capability) to be attained by combining a UV absorbent and a water-soluble polymer was evaluated by testing low-viscosity samples each having the composition shown in Tables 2 and 3 below. In Tables 2 and 3, "Control Example" is a system containing a UV absorbent but not containing a water-soluble polymer; and "Example" is a system containing both a UV absorbent and a water-soluble polymer as combined.

<UV Protective Enhancing Effect>
(Test Method)

Each sample was applied on a coating substrate in a ratio of 2 mg/cm$^2$, and using a spectrometer ("U-4100" by Hitachi High-Technologies Corpoaration), the UV absorbance (abs.) at the maximum absorption wavelength (λmax) (nm) in the ultraviolet absorption spectrum of the UV absorbent in the sample was measured. The found data are shown in Tables 2 and 3. The sample having a larger UV absorbance value is more excellent in the UV protective effect. λmax (nm) of the UV absorbent in each sample is shown in Table 1 below.

TABLE 1

| Sample | UV Absorbent Incorporated | λmax (nm) |
| --- | --- | --- |
| Control Example 1, Examples 1A and 1B Control Example 7, Example 7 | Octyl Methoxycinnamate | 311 |
| Control Example 2, Examples 2A and 2B | Octocrylene | 303 |
| Control Example 3, Examples 3A and 3B | Dimethicodiethylbenzal Malonate | 312 |
| Control Example 4, Examples 4A and 4B Control Example 8, Example 8 | Phenylbenzimidazolesulfonic Acid | 302 |
| Control Example 5, Examples 5A and 5B | Disodium Phenyldibenzimidazoletetrasulfonate | 335 |
| Control Example 6, Examples 6A and 6B | Methylene-bis-benzotriazolyl-tetramethylbutylphenol | 364 |

(UV Absorption Capability Increase Rate)

The increase rate of the UV absorbance (abs.) in each Example relative to that in Control Example was computed from the found data. Example and Control Example both using the same UV absorbent were compared with each other. The results are shown in Tables 2 and 3.

(UV Protective Effect)

From the above-mentioned UV absorption capability increase rate in each Example, the UV protective effect was evaluated according to the following standards.

A++: The UV absorption capability increase rate was higher by more than 20% than that in Control Example.
A+: The UV absorption capability increase rate was higher by from more than 10% to 20% than that in Control Example.
A: The UV absorption capability increase rate was higher by from more than 5% to 10% than that in Control Example.
B: The UV absorption capability increase rate was higher by from more than 0% to 5% than that in Control Example.
C: The UV absorption capability increase rate was the same as or lower than that in Control Example.

<Viscosity>

The prepared sample was shaken, and its viscosity was measured with a B-type viscometer ("Vismetron Viscometer" by Shibaura Systems Co., Ltd., rotation number 12 rpm) at 30° C.

TABLE 2

| | Contr. Ex. 1 | Ex. 1A | Ex. 1B | Contr. Ex. 2 | Ex. 2A | Ex. 2B | Contr. Ex. 3 | Ex. 3A | Ex. 3B | Contr. Ex. 4 | Ex. 4A | Ex. 4B |
|---|---|---|---|---|---|---|---|---|---|---|---|---|
| Decamethylcyclopentasiloxane | 47 | 47 | 47 | 47 | 47 | 47 | 47 | 47 | 47 | 47 | 47 | 47 |
| Lauryl PEG-9 Polydimethylsiloxyethyldimethicone | 1 | 1 | 1 | 1 | 1 | 1 | 1 | 1 | 1 | 1 | 1 | 1 |
| Diisopropyl Sebacate | 2 | 2 | 2 | 2 | 2 | 2 | 2 | 2 | 2 | 2 | 2 | 2 |
| 2-Ethylhexyl 2-Ethylhexanoate | 2 | 2 | 2 | 2 | 2 | 2 | 2 | 2 | 2 | 2 | 2 | 2 |
| Hydrophobicated (Silane-treated) Cation-processed Zinc Oxide | 15 | 15 | 15 | 15 | 15 | 15 | 15 | 15 | 15 | 15 | 15 | 15 |
| Octyl Methoxycinnamate | 3 | 3 | 3 | — | — | — | — | — | — | — | — | — |
| Octocrylene | — | — | — | 3 | 3 | 3 | — | — | — | — | — | — |
| Dimethicodiethylbenzal malonate(*1) | — | — | — | — | — | — | 3 | 3 | 3 | — | — | — |
| Phenylbenzimidazolesulfonic acid(*2) | — | — | — | — | — | — | — | — | — | 3 | 3 | 3 |
| Disodium Phenyldibenzimidazoletetrasulfonate(*3) | — | — | — | — | — | — | — | — | — | — | — | — |
| Methylenebisbenzotriazolyltetramethylbutylphenol(*4) | — | — | — | — | — | — | — | — | — | — | — | — |
| Triethanolamine | — | — | — | — | — | — | — | — | — | 1.8 | 1.8 | 1.8 |
| Agar | — | 0.6 | — | — | 0.6 | — | — | 0.6 | — | — | 0.6 | — |
| Succinoglycan | — | — | 0.6 | — | — | 0.6 | — | — | 0.6 | — | — | 0.6 |
| Ion-Exchanged Water | 27.05 | 26.45 | 26.45 | 27.05 | 26.45 | 26.45 | 27.05 | 26.45 | 26.45 | 25.25 | 24.65 | 24.65 |
| EDTA-3Na•2H$_2$O | 0.05 | 0.05 | 0.05 | 0.05 | 0.05 | 0.05 | 0.05 | 0.05 | 0.05 | 0.05 | 0.05 | 0.05 |
| Glycerin | 2.55 | 2.55 | 2.55 | 2.55 | 2.55 | 2.55 | 2.55 | 2.55 | 2.55 | 2.55 | 2.55 | 2.55 |
| Phenoxyethanol | 0.35 | 0.35 | 0.35 | 0.35 | 0.35 | 0.35 | 0.35 | 0.35 | 0.35 | 0.35 | 0.35 | 0.35 |
| Viscosity (mPa·s/30° C.) | 1,040 | 930 | 700 | 600 | 600 | 660 | 1,260 | 1,010 | 620 | 1,730 | 3,400 | 740 |
| UV Absorption Capability (abs.) | 1.318 | 1.507 | 1.771 | 1.124 | 1.304 | 1.319 | 1.264 | 1.32 | 1.303 | 1.026 | 1.311 | 1.076 |
| UV Absorption Capability Increase Rate (abs. increase rate, relative to Control Example) (%) | — | 14.3 | 34.4 | — | 16.0 | 17.3 | — | 4.4 | 3.1 | — | 27.8 | 4.9 |
| UV Protective Enhancing Effect (relative to Control Example) | — | A+ | A++ | — | A+ | A+ | — | B | B | — | A++ | B |

TABLE 3

| | Contr. Ex. 5 | Ex. 5A | Ex. 5B | Contr. Ex. 6 | Ex. 6A | Ex. 6B | Contr. Ex. 7 | Ex. 7 | Contr. Ex. 8 | Ex. 8 |
|---|---|---|---|---|---|---|---|---|---|---|
| Decamethylcyclopentasiloxane | 47 | 47 | 47 | 47 | 47 | 47 | 47 | 47 | 47 | 47 |
| Lauryl PEG-9 Polydimethylsiloxyethyldimethicone | 1 | 1 | 1 | 1 | 1 | 1 | 2.5 | 2.5 | 2.5 | 2.5 |
| Diisopropyl Sebacate | 2 | 2 | 2 | 2 | 2 | 2 | 2 | 2 | 2 | 2 |
| 2-Ethylhexyl 2-Ethylhexanoate | 2 | 2 | 2 | 2 | 2 | 2 | 2 | 2 | 2 | 2 |
| Hydrophobicated (Silane-treated) Cation-processed Zinc Oxide | 15 | 15 | 15 | 15 | 15 | 15 | — | — | — | — |
| Octyl Methoxycinnamate | — | — | — | — | — | — | 3 | 3 | — | — |
| Octocrylene | — | — | — | — | — | — | — | — | — | — |
| Dimethicodiethylbenzal malonate[*1] | — | — | — | — | — | — | — | — | — | — |
| Phenylbenzimidazolesulfonic acid[*2] | — | — | — | — | — | — | — | — | 3 | 3 |
| Disodium Phenyldibenzimidazoletetrasulfonate[*3] | 3 | 3 | 3 | — | — | — | — | — | — | — |
| Methylenebis-benzotriazolyl-tetramethylbutylphenol[*4] | — | — | — | 3 | 3 | 3 | — | — | — | — |
| Triethanolamine | 1.8 | 1.8 | 1.8 | — | — | — | — | — | 1.8 | 1.8 |
| Agar | — | 0.6 | — | — | 0.6 | — | — | 0.6 | — | 0.6 |
| Succinoglycan | — | — | 0.6 | — | — | 0.6 | — | — | — | — |
| Ion-Exchanged Water | 25.25 | 24.65 | 24.65 | 27.05 | 26.45 | 26.45 | 40.1 | 39.5 | 38.3 | 37.7 |
| EDTA-3Na·2H$_2$O | 0.05 | 0.05 | 0.05 | 0.05 | 0.05 | 0.05 | 0.05 | 0.05 | 0.05 | 0.05 |
| Glycerin | 2.55 | 2.55 | 2.55 | 2.55 | 2.55 | 2.55 | 3.0 | 3.0 | 3.0 | 3.0 |
| Phenoxyethanol | 0.35 | 0.35 | 0.35 | 0.35 | 0.35 | 0.35 | 0.35 | 0.35 | 0.35 | 0.35 |
| Viscosity (mPa·s/30° C.) | 500 | 870 | 470 | 2,500 | 2,990 | 1,210 | 42.5 | 40.0 | 45.0 | 40.0 |
| UV Absorption Capability (abs.) | 0.901 | 1.024 | 0.922 | 0.955 | 1.018 | 1.001 | 1.082 | 1.225 | 0.351 | 0.403 |
| UV Absorption Capability Increase Rate (abs. increase rate, relative to Control Example) (%) | — | 13.7 | 2.3 | — | 6.6 | 4.8 | — | 13.2 | — | 14.8 |
| UV Protective Enhancing Effect (relative to Control Example) | — | A$^+$ | B | — | A | B | — | A$^+$ | — | A$^+$ |

In Tables 2 and 3, as the compounds mentioned below, the commercial products mentioned below were used.

Dimethicodiethylbenzalmalonate[*1]: "Parsol SLX" (by DSM Nutrition Japan K.K.);

Phenylbenzimidazolesulfonicacid[*2]: "Eusolex 232" (by Merck & Co., Inc.);

Disodium Phenyldibenzimidazoletetrasulfonate[*3]: "Neo Heliopan AP" (by Haarmann & Reimer);

Methylenebis-benzotriazolyl-tetramethylbutylphenol[*4]: "Tinosorb M" (by Ciba Speciality Chemicals Inc.).

As obvious from the results in Tables 2 and 3, it has been confirmed that, in the case where a UV absorbent having a UV absorption wavelength region both in the UV-A region (320 to 400 nm) and in the UV-B region (290 to 320 nm) is used, the UV absorbent can exhibit the UV protective enhancing effect thereof when used in combination with a water-soluble polymer, as compared with the case where the UV absorbent is used alone.

2. Feeling in Use

Example 9, Control Example 9

Example 9 (formulation with agar) and Control Example 9 (formulation without agar) each having the composition shown in Table 4 were monitored and compared with each other by women panelists (10 persons) in point of the feeling in use thereof.

With respect to the evaluation items, the samples were evaluated as to whether or not the felling in use of the sample of Example 9 could be bettered than that of the sample of Control Example 9, based on the following evaluation standards. The results are shown in Table 5. No panelist answered that the feeling in use of the sample of Example 9 was worse than that of the sample of Control Example 9.

(Evaluation Standards)

A$^+$: Seven or more of 10 panelists confirmed the improvement.

A: Five or more of 10 panelists confirmed the improvement.

B: Three or more of 10 panelists confirmed the improvement.

C: Two or less of 10 panelists confirmed the improvement.

TABLE 4

| | Ex. 9 | Contr. Ex. 9 |
|---|---|---|
| Dimethyldistearylammonium hectorite | 0.15 | 0.15 |
| Decamethylcyclopentasiloxane | 45.8 | 45.8 |
| Lauryl PEG-9 Polydimethylsiloxyethyldimethicone | 0.6 | 0.6 |
| Trimethylsiloxysilicic Acid | 0.05 | 0.05 |
| Polyoxybutylene Polyoxypropylene Glycol | 0.1 | 0.1 |
| 2-Ethylhexyl 2-Ethylhexanoate | 2 | 2 |
| Isostearic Acid | 0.3 | 0.3 |
| Octyl Methoxycinnamate | 5 | 5 |
| Octocrylene | 1 | 1 |
| Hydrophobicated (Silane-treated) Cation-processed Zinc Oxide | 20 | 20 |
| Phenylbenzimidazolesulfonic Acid | 1.5 | 1.5 |
| Triethanolamine | 0.9 | 0.9 |
| Ion-Exchanged Water | 21.2 | 22.2 |
| Trisodium Edetate | 0.05 | 0.05 |
| Agar | 1 | — |
| Phenoxyethanol | 0.35 | 0.35 |

TABLE 5

| Evaluation Item | Evaluation (Improvement of the Feeling in use in Example 9) |
|---|---|
| Fitting feel during application | A |
| Smooth feel after application | A$^+$ |

TABLE 5-continued

| Evaluation Item | Evaluation (Improvement of the Feeling in use in Example 9) |
|---|---|
| Dry feel after application | A+ |
| Non-sticky feel after application | A |
| Non-filmy feel after application | A |

As obvious from the results shown in Table 5, it has been confirmed that the feeling in use of the sample of Example 9 with agar (water-soluble polymer) incorporated therein is bettered than that of the sample of Control Example with no agar therein.

Formulation Examples are shown below.

Example 10

Water-in-oil Emulsion Sunscreen Skin Milk

| (Ingredients) | (% by mass) |
|---|---|
| (1) Decamethylcyclopentasiloxane | 15 |
| (2) Polyoxyethylene/methylpolysiloxane copolymer | 1 |
| (3) Olefin oligomer | 10 |
| (4) Dimethylpolysiloxane | 2 |
| (5) Fragrance | q.s. |
| (6) Tris(polypropylene glycol-3 benzyl ether) citric acid | 5 |
| (7) Diisopropyl sebacate | 5 |
| (8) 4-Tert-butyl-4'-methoxydibenzoylmethane | 2.5 |
| (9) Organic-modified clay mineral | 0.1 |
| (10) Hydrophobicated (silane-treated) cation-processed zinc oxide | 15 |
| (11) Spherical resin fine particle powder ("Ganzpearl" by Ganz Chemical) | 3 |
| (12) Ion-exchanged water | bal. |
| (13) Glycerin | 3 |
| (14) Agar | 1 |
| (15) Edetic acid salt | q.s. |
| (16) Phenoxyethanol | 0.5 |

(Production Method)

(7) and (8) are mixed and dissolved at 80° C., and added to the oily phase of (1) to (6). Next, (9) to (11) are added thereto, and dispersed and mixed with a disperser. (12) to (16) are mixed, heated and dissolved at 95° C., and then gradually added to the oily phase with stirring with a disperser, and after fully uniformly mixed, this is rapidly cooled down to 25° C. to prepare the intended sunscreen skin milk.

Example 11

Water-in-oil Emulsion Sunscreen Skin Milk

| (Ingredients) | (% by mass) |
|---|---|
| (1) Trimethylsiloxysilicic acid | 0.2 |
| (2) Polyoxyethylene/methylpolysiloxane copolymer | 1.5 |
| (3) Light isoparaffin | 15 |
| (4) Tetraisobutane | 15 |
| (5) Dimethylpolysiloxane | 3 |
| (6) Fragrance | q.s. |
| (7) 2-Ethylhexyl 2-ethylhexanoate | 2 |
| (8) Octyl methoxycinnamate | 5 |
| (9) Octocrylene | 2 |
| (10) Hydrophobicated (silane-treated) cation-processed zinc oxide | 18 |
| (11) Crosslinked silicone/network-structured silicone copolymer | 2 |
| (12) Ion-exchanged water | bal. |
| (13) Glycerin | 3 |
| (14) Agar | 0.5 |
| (15) Edetic acid salt | q.s. |
| (16) Phenoxyethanol | 0.3 |

(Production Method)

(1) to (11) are dispersed and mixed with a disperser. (12) to (16) are mixed, heated and dissolved at 95° C., and then gradually added to the oily phase with stirring with a disperser, and after fully uniformly mixed, this is rapidly cooled down to 25° C. to prepare the intended sunscreen skin milk.

Example 12

Water-in-oil Emulsion Sunscreen Skin Milk

| (Ingredients) | (% by mass) |
|---|---|
| (1) Trimethylsiloxysilicic acid | 0.2 |
| (2) Polyoxyethylene/methylpolysiloxane copolymer | 1.5 |
| (3) Cyclomethicone | 30 |
| (4) Dimethylpolysiloxane | 3 |
| (5) Fragrance | q.s. |
| (6) 2-Ethylhexyl 2-ethylhexanoate | 2 |
| (7) Octyl methoxycinnamate | 5 |
| (8) Octocrylene | 2 |
| (9) Hydrophobicated (silane-treated) cation-processed zinc oxide | 18 |
| (10) Crosslinked silicone/network-structured silicone copolymer | 2 |
| (11) Ion-exchanged water | bal. |
| (12) Glycerin | 2 |
| (13) Succinoglycan | 0.5 |
| (14) Edetic acid salt | q.s. |
| (15) Phenoxyethanol | 0.3 |

(Production Method)

(1) to (10) are dispersed and mixed with a disperser. (11) to (15) are mixed and dissolved, and then gradually added to the oily phase with stirring with a disperser to thereby prepare the intended sunscreen skin milk.

Example 13

Multiphase Sunscreen Skin Milk

| (Ingredients) | (% by mass) |
|---|---|
| (1) Polyoxyethylene-hardened castor oil | 0.5 |
| (2) Isostearic acid | 0.2 |
| (3) Diisopropyl sebacate | 5 |
| (4) 4-(1,1-Dimethylethyl)-4'-methoxydibenzoylmethane | 2 |
| (5) Tris(polypropylene glycol-3 benzyl ether)citric acid | 5 |
| (6) Decamethylcyclopentasiloxane | 25 |
| (7) Polyoxybutylene polyoxypropylene glycol | 2 |
| (8) Dimethyldistearylammonium hectorite | 0.5 |
| (9) Hydrophobicated zinc oxide | 10 |
| (10) Silicone resin fine particle powder ("Tospearl 2000B", by Momentive Performance Materials) | 2 |
| (11) Citric acid | 0.04 |
| (12) Sodium citrate | 0.06 |

-continued

| (Ingredients) | (% by mass) |
|---|---|
| (13) Dipropylene glycol | 2 |
| (14) Methylglucose | 1 |
| (15) Dynamite glycerin | 1 |
| (16) Edible salt | 0.1 |
| (17) Succinoglycan | 0.5 |
| (18) Phenoxyethanol | q.s. |
| (19) Ion-exchanged water | bal. |

(Production Method)

The oily phase of (1) to (4) is gradually added to the aqueous phase of (11) to (19) to give an O/W preparation. The preparation is gradually added to the oily phase of (5) to (10), and stirred with a homomixer to prepare the intended sample.

Example 14

Water-in-oil Emulsion Foundation

| (Ingredients) | (% by mass) |
|---|---|
| (1) Decamethylcyclopentasiloxane | 10 |
| (2) Dodecamethylcyclohexasiloxane | 20 |
| (3) Trimethylsiloxysilicic acid | 1 |
| (4) Poly(oxyethylene-oxypropylene)/methylpolysiloxane copolymer | 3 |
| (5) Octyl methoxycinnamate | 5 |
| (6) Isostearic acid | 0.5 |
| (7) Alkyl-modified silicone resin-coated titanium dioxide | 10 |
| (8) Dextrin palmitate-coated titanium dioxide | 5 |
| (9) Dextrin palmitate-coated talc | 5 |
| (10) Needle-like fine particles of titanium dioxide | 1 |
| (11) Dextrin palmitate-coated red iron oxide | 0.5 |
| (12) Dextrin palmitate-coated yellow iron oxide | 1.6 |
| (13) Dextrin palmitate-coated black iron oxide | 0.1 |
| (14) Spherical silicic anhydride | 5 |
| (15) Silicic anhydride-coated mica | 1 |
| (16) Sodium citrate | q.s. |
| (17) *Sophora flavescens* extract | 1 |
| (18) Agar | 0.5 |
| (19) Pure water | bal. |

(Production Method)

Using a disperser, (7) to (13) are dispersed and mixed and added to the oily phase prepared by mixing (1) to (6) with a disperser. (14) to (19) are mixed, heated and dissolved at 95° C., and then gradually added to the oily phase with stirring with a disperser, and after fully uniformly mixed, this is rapidly cooled down to 25° C. to prepare the intended emulsion foundation.

INDUSTRIAL APPLICABILITY

The low-viscosity water-in-oil emulsion sunscreen cosmetic composition of the present invention is extremely excellent in enhancing UV protective effect over a broad UV radiation region and has superior feeling in use (smooth feeling, dry feeling, and non-sticky, etc.).

The invention claimed is:

1. A water-in-oil emulsion sunscreen cosmetic composition comprising (a) from 0.05 to 5% by mass of agar and/or succinoglycan and (b) from 0.01 to 30% by mass of an ultraviolet absorbent, and having a viscosity of at most 10,000 mPa·s (as measured with a B-type viscometer at 30° C.), wherein the aqueous phase accounts for at most 45% by mass, the aqueous phase is dispersed in an oil phase, and component (a) is incorporated in the dispersed aqueous phase.

2. The water-in-oil emulsion sunscreen cosmetic composition as claimed in claim 1, which is a two-layer separation-type cosmetic composition to be used after shaking before use.

3. A water-in-oil emulsion sunscreen cosmetic composition comprising (a) from 0.01 to 10% by mass of a water-soluble polymer selected from the group consisting of plant-derived water-soluble polymers and microorganism-water-soluble polymers and (b) from 0.01 to 30% by mass of an ultraviolet derived absorbent, and having a viscosity of at most 10,000 mPa·s (as measured with a B-type viscometer at 30° C.), wherein the aqueous phase accounts for at most 45% by mass, the aqueous phase is dispersed in an oil phase, and component (a) is incorporated in the dispersed aqueous phase.

4. The water-in-oil emulsion sunscreen cosmetic composition as claimed in claim 3, wherein component (a) is selected from the group consisting of agar and succinoglycan.

5. The water-in-oil emulsion sunscreen cosmetic composition as claimed in claim 3, wherein component (a) is agar.

6. The water-in-oil emulsion sunscreen cosmetic composition as claimed in claim 3, wherein component (a) is succinoglycan.

7. The water-in-oil emulsion sunscreen cosmetic composition as claimed in claim 1, which is a two-layer separation-type cosmetic composition to be used after shaking before use.

8. The water-in-oil emulsion sunscreen cosmetic composition as claimed in claim 1, wherein component (b) is any one or more selected from among oil-soluble UV absorbents and water-soluble absorbents.

9. The water-in-oil emulsion sunscreen cosmetic composition as claimed in claim 1, wherein component (b) is any one or more selected from among benzoic acid-type UV absorbents, anthranilic acid-type UV absorbents, salicylic acid-type ultraviolet absorbents, cinnamic acid-type UV absorbents, 2-phenyl-5-methylbenzoxazole, 2,2'-hydroxy-5-methylphenylbenzotriazole, 2-(2'-hydroxy-5'-t-octylphenyl)benzotriazole, 2-(2'-hydroxy-5'-methylphenylbenzotriazole), dibenzaladine, dianisoylmethane, 4-tert-butyl-4'-methoxydibenzoylmethane, 4-(1,1-dimethylethyl)-4'-methoxydibenzoylmethane, 5-(3,3-dimethyl-2-norbornylidene)-3-pentan-2-one, octocrylene [=2-ethylhexyl 2-cyano-3,3-diphenyl-2-propenoate], and Polysilicone-15 [=dimethicodiethylbenzal malonate].

10. The water-in-oil emulsion sunscreen cosmetic composition as claimed in claim 1, wherein component (b) is any one or more selected from among benzophenone-type UV absorbents, benzimidazole-type UV absorbents, benzotriazole-type UV absorbents, 3-(4'-methylbenzylidene)-d,l-camphor, 3-benzylidene-d,l-camphor, urocanic acid, and ethyl urocanoate.

11. The water-in-oil emulsion sunscreen cosmetic composition as claimed in claim 1, wherein component (a) comprises succinoglycan.

* * * * *